(12) United States Patent
Kambin

(10) Patent No.: US 6,596,008 B1
(45) Date of Patent: Jul. 22, 2003

(54) METHOD AND INSTRUMENTS FOR PERCUTANEOUS ARTHROSCOPIC DISC REMOVAL, BONE BIOPSY AND FIXATION OF THE VERTEBRAL

(76) Inventor: Parviz Kambin, 239 Chester Rd., Devon, PA (US) 19333

(*) Notice: Subject to any disclaimer, the term of this patent is extended or adjusted under 35 U.S.C. 154(b) by 407 days.

(21) Appl. No.: 09/711,614

(22) Filed: Nov. 13, 2000

Related U.S. Application Data

(60) Division of application No. 09/370,318, filed on Aug. 9, 1999, now Pat. No. 6,175,758, which is a continuation-in-part of application No. 08/893,286, filed on Jul. 15, 1997, now Pat. No. 5,964,761.

(51) Int. Cl.$^7$ .............................................. A61B 17/00
(52) U.S. Cl. .......................... 606/190; 606/61; 606/96; 604/164.01
(58) Field of Search ............................. 606/60, 61, 96, 606/104, 108, 190; 128/898; 604/164.01

(56) References Cited

U.S. PATENT DOCUMENTS

| | | |
|---|---|---|
| 4,545,374 A | 10/1985 | Jacobson |
| 4,573,448 A | 3/1986 | Kambin |
| 4,583,538 A | 4/1986 | Onik et al. |
| 5,242,443 A | 9/1993 | Kambin |
| 5,395,317 A | 3/1995 | Kambin |
| 5,480,440 A | 1/1996 | Kambin |
| 5,540,690 A | 7/1996 | Miller et al. |
| 5,752,955 A | 5/1998 | Errico |
| 6,021,342 A | 2/2000 | Braband |
| 6,064,904 A | 5/2000 | Yanof et al. |

OTHER PUBLICATIONS

P. Kambin, "Posterolateral Percutaneous Lumbar Interbody Fusion", *Arthroscopic Microdisectomy: Minimal Intervention in Spinal Surgery*, pp. 117–121 (1991).

P. Kambin, " Arthroscopic Lumbar Intervertebral Fusion", *The Adult Spine: Principles and Practice*, Chapter 95, pp. 2037–2046 (1997).

F.R. Magerl, "Stabilization of the Lower Thoracic and Lumbar Spine with External Skeletal Fixation", *Clinical Orthopedics and Related Research*, pp. 125–141 (Oct. 1984).

H.F. Leu et al. "Percutaneous Lumbar Restabilizaiton", *Arthroscopic Microdisectomy: Minimal Intervention in Spinal Surgery*, pp. 123–125 (1991).

P. Kambin, "Arthroscopic Lumbar Interbody Fusion", *Spine Care*, Chapter 77, vol. 2 (1997).

P. Kambin, "Arthroscopic Techniques for Spinal Surgery", *Operative Arthroscopy*, $2^{nd}$ Edition, pp. 1215–1225 (1996).

P. Kambin et al. "Arthroscopic Fusion of the Lumbosacral Spine", Lumbosacral and Spinopelvic Fixation, Chapter 44, pp. 565–577 (1996).

H.F. Leu et al., "Percutaneous Fusion of the Lumbar Spine: A Promising Technique", Spine: Sate of the Arts Review 6, pp. 593–604 (Sep. 1992).

H.F. Leu et al., "Lumbar Percutaneous Endoscopic Interbody Fusion", Clinical Orthopedics and Related Research 337:58–63 (Apr. 1997).

*Primary Examiner*—David O. Reip
(74) *Attorney, Agent, or Firm*—Howson & Howson

(57) ABSTRACT

The insertion points for guide pins used in percutaneous vertebral fixation by pedicle screw are determined by establishing an approach path on a CT image, measuring on the CT image the distance from the intersection of the approach path and the skin of the patient's back to the patient's midline, and marking off the corresponding distance while visualizing the patient by anteroposterior fluoroscopy. An longitudinally expansible pedicle screw comprises a shaft with bone-engaging threads on a distal portion, machine screw threads on a proximal portion, and a tubular extension having wrench-engageable holes on a proximal face, and internal threads engaging the machine screw threads on the proximal portion of the shaft. An oval cannula accommodates an arthroscope and forceps simultaneously for intervertebral disc surgery.

13 Claims, 6 Drawing Sheets

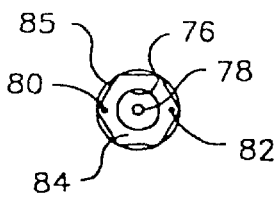
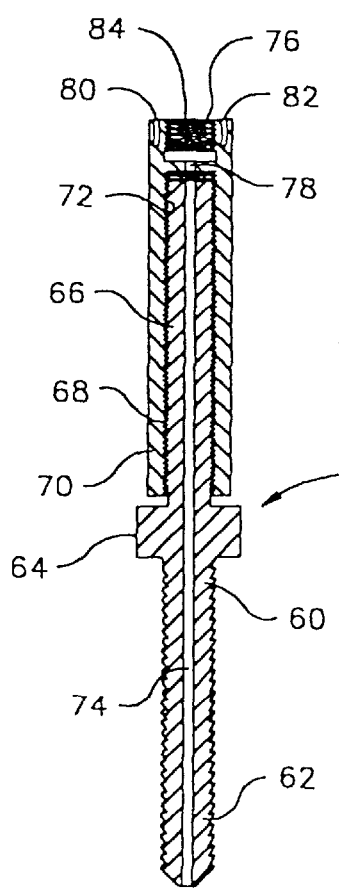
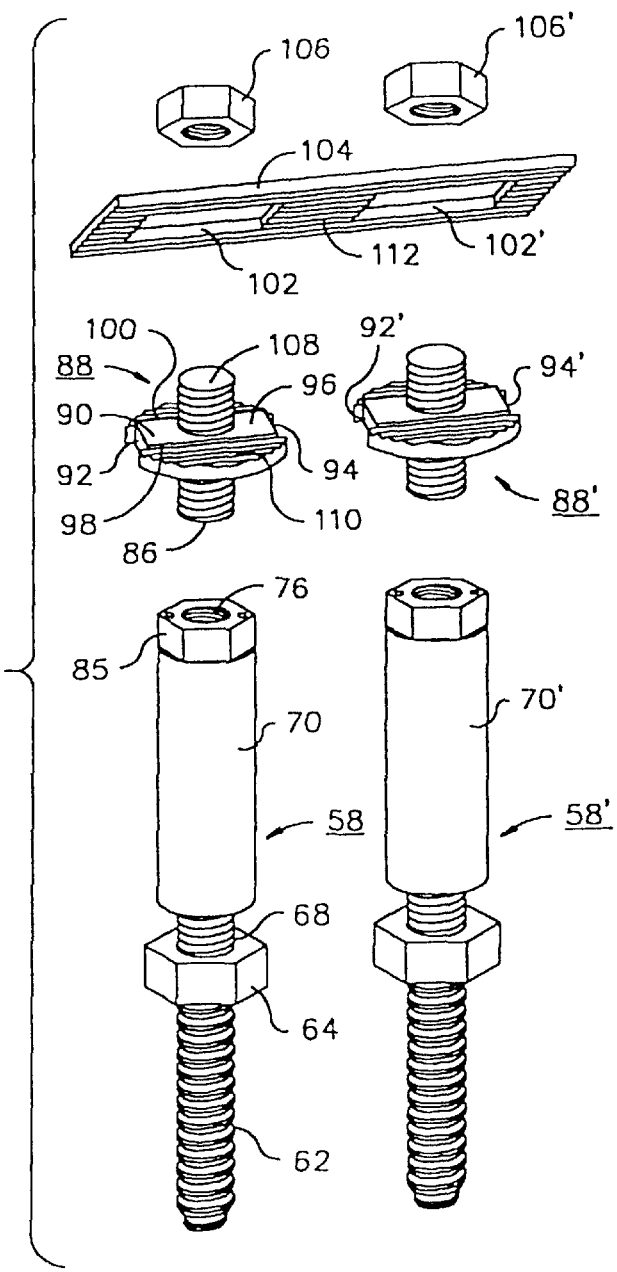

*Fig. 9* *Fig. 10* *Fig. 11*
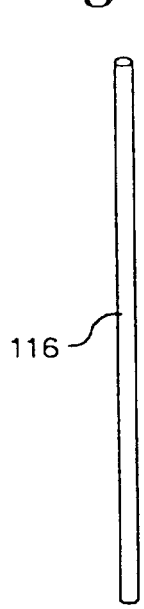
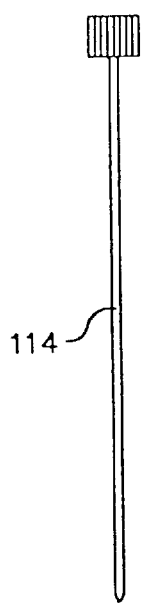
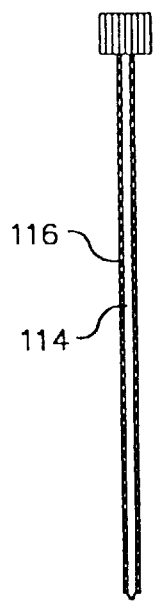
*Fig. 17*
*Fig. 12* *Fig. 14* *Fig. 16*
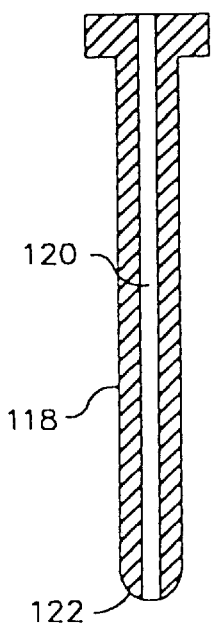
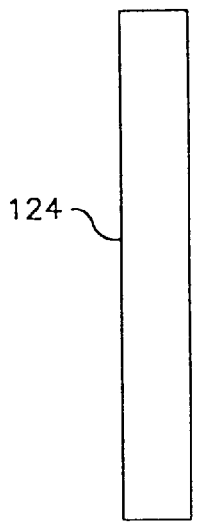
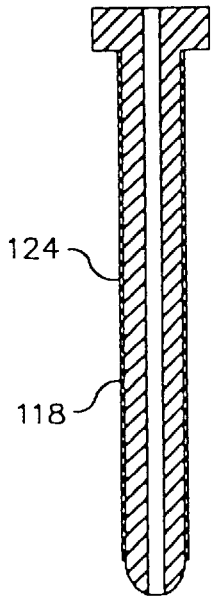
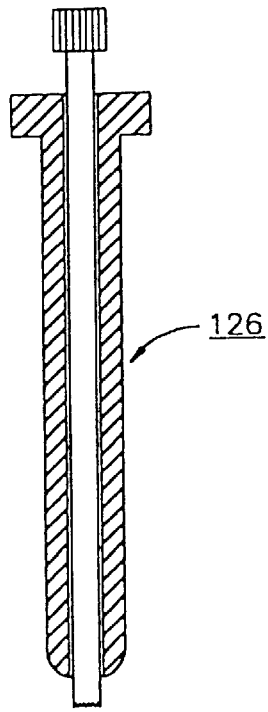
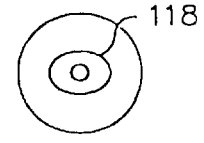
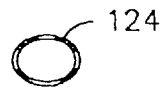
*Fig. 13* *Fig. 15*

METHOD AND INSTRUMENTS FOR PERCUTANEOUS ARTHROSCOPIC DISC REMOVAL, BONE BIOPSY AND FIXATION OF THE VERTEBRAL

CROSS REFERENCE TO RELATED APPLICATION

This is a division of application Ser. No. 09/370,318, filed Aug. 9, 1999, now U.S. Pat. No. 6,175,758, which is a continuation-in-part of application Ser. No. 08/893,286, filed Jul. 15, 1997, now U.S. Pat. No. 5,964,761.

SUMMARY OF THE INVENTION

This invention relates generally to surgery, and more particularly to methods and instrumentation having their principal utility in spinal surgery.

My U.S. Pat. Nos. 5,242,443, dated Sep. 7, 1993 and 5,480,440, dated Jan. 2, 1996, the disclosures of which are here incorporated by reference, describe a surgical technique for percutaneous fixation of two or more adjacent vertebrae by means of screws inserted percutaneously into the pedicles of the vertebrae and secured together by links located just under the skin of the patient's back. The technique avoids the many difficulties encountered in conventional internal and external vertebral fixation.

In vertebral fixation according to the methods described in my prior patents, a cannulated tubular guide is maneuvered into alignment with the pedicle. A pin is introduced through the guide and tapped with a mallet so that it enters the cortical bone at the junction of the base of the transverse process and the proximal articular process. The guide is then removed and a cannulated obturator is placed over the pin. An access cannula is then placed over the obturator and advanced to the pedicle. The obturator is then removed from the access cannula and a cannulated drill is advanced over the pin and operated to form an entrance into the medullary canal of the pedicle. A probe is then advanced into the medullary canal to create a bore into the vertebral body. The bore may then be tapped to form threads engageable by a pedicle screw, or alternatively a self-tapping pedicle screw can be inserted. With pedicle screws threaded into pedicles of adjacent vertebrae, adapters of the appropriate length are selected and secured to the proximal ends of the screws. The screws, with the adapters attached to them, are connected by links located just underneath the patient's skin. The procedure is much less invasive than conventional internal fixation, minimizes damage to muscle tissue and ligaments, reduces recovery and rehabilitation time, and simplifies removal of the fixation appliances. The procedure also reduces the infection risks, and avoids the physical limitations, imposed on the patient by external fixation.

The placement of a plate or rod under the skin, following commonly practiced open spinal fusion and pedicular screw insertion, facilitates subsequent retrieval of the hardware when the fusion and stabilization are accomplished. This eliminates the need for a second operation for access to, and retrieval of, the deeply positioned hardware.

The internal diameter of the medullary canal of the lumbar pedicles is typically only about 7 to 8 mm. The small size of the medullary canal mandates precise positioning of screws in the pedicle. To achieve proper alignment of the cannulated tubular guide with the axis of the pedicle, the guide is visualized fluoroscopically as it is being inserted. When properly aligned, the guide appears as an opaque circle in the center of the pedicle. A similar fluoroscopic method is used for alignment of the screw with the pedicle, the screw appearing as a dot in the center of the pedicle when properly aligned. This method is referred to as the "bulls-eye" method.

Conventional bulls-eye alignment has proven to be less than entirely reliable for proper positioning of percutaneously inserted guides and screws for several reasons. First, the operation is carried out using a radiolucent table and a C-arm fluoroscope. To allow better visualization of the pedicles the table is tilted away from the C-arm, or alternatively, the C-arm is tilted relative to the table. The angle of tilt of the C-arm fluoroscope relative to the operating table affects the angle of the guide or screw. Therefore, accurate measurement of the necessary tilt of the C-arm to accommodate the desired angle of insertion of the guide or screw is necessary. A second deficiency of the conventional bulls-eye alignment method arises because the skin entry point plays a significant role in the proper positioning of the guide at the center of the pedicle and the insertion of the probe into the vertebral body. A third deficiency of the bullseye method is that the distance between the guide and the x-ray tube can have an effect on the position of the guide relative to the pedicle. If the x-ray tube is too close to the patient and the angle of the tilt of the C-arm has not been predetermined and measured, the peripheral x-ray beams may present a distorted view of the position of the guide. A fourth deficiency of the bulls-eye method is that, when the C-arm is tilted by 20° to 30°, clear visualization of the boundaries of the pedicles is difficult.

Similar difficulties are encountered in positioning a biopsy cannula for taking a vertebral biopsy. An important object of this invention, therefore, is to provide a more accurate and reliable method for establishing an insertion point for a percutaneously inserted instrument for spinal surgery.

A method for determining the point for insertion of an instrument in a percutaneous spinal procedure in accordance with the invention, comprises the following steps. The patient is scanned by computed tomography, and an image is produced of an axial plane through the patient, i.e. a plane perpendicular to the long axis of the patient's body. On that image, a desired path for insertion of a guide pin is determined, and the lateral distance from the patient's midline to the point at which said path intersects the skin of the patient's back is determined. By viewing the patient's spine radiographically in the anterior-posterior direction, the skin of the patient's back is marked directly over the midline, and marking the skin of the patient's back is also marked with a line extending transverse to the patient's midline in a plane corresponding to the transverse plane in which the computed tomography scan was taken. Thereafter, an insertion point is established on the patient's back, on the transverse line, at a distance equal to the lateral distance measured on the image.

Another important object of this invention, therefore, is to provide an more accurate and reliable method for placement of a guide in the center of a pedicle in preparation for the insertion of a pedicle screw or biopsy cannula.

In accordance with the invention, the insertion points and insertion angles for the guide pins are established by a technique using a combination of computed tomography and conventional radiographic visualization. CT scans of the patient are taken in axial planes through the pedicles of two or more vertebrae to be fixated. Using the CT images, a desired path for insertion of a guide pin into each of these vertebrae is established. The angle of the path relative to the median plane is measured on the CT image for each of the vertebrae. Also, for each of these vertebrae, a measurement is made, on the CT image thereof, of the lateral distance from the patient's midline to the point at which the insertion path intersects the skin of the patient's back. By viewing the patient's spine radiographically in the anterior-posterior direction, a marking is made on the skin of the patient's back directly over the midline, and a transverse line is drawn for each of the vertebrae to be fixated over the centers of a pedicle thereof. Then, for each of the vertebrae to be fixated, an insertion point is established on the patient's back, on the corresponding transverse line, at a distance equal to the lateral distance measured on the CT image thereof. Thereafter a guide pin is inserted through the patient's back, and into a pedicle of each of the vertebrae to be fixated, through the insertion point established therefor and at the angle measured therefor.

Another problem with the method of percutaneous fixation as described in my prior patents is that the adapters that are attached to the proximal ends of the pedicle screws need to be available in a variety of sizes so that, during surgery, pedicle screws of the appropriate lengths can be selected to position the connecting link at the proper position just underneath the patient's skin. Often the available adapters are either too long or to short to allow proper positioning of the connecting links. Moreover, during surgery, the attachment of the adapter to the screw is time consuming and at times difficult. Removal and reinsertion of adapters in an effort to find one of the proper length can also result in loosening and displacement of the pedicle screw. Still further objects of the invention, therefore, are to simplify the procedure for vertebral fixation by eliminating the need for various different sizes of adapters, to allow easier and more precise positioning of the connecting links, and to reduce the likelihood of loosening or displacement of pedicle screws.

In accordance with the invention, the step of inserting a guide pin through the patient's back is followed by the step of introducing a lengthwise expansible pedicle screw, having proximal and distal ends, into the pedicle of each of the two or more vertebrae to be fixated. When each screw is properly introduced, its distal end is located inside the vertebra and its proximal end is located underneath the fascia of the patient's back. Each screw is then expanded lengthwise until its proximal end is located adjacent to the fascia, but underneath the skin. The proximal ends of the pedicle screws are then rigidly connected together by connecting means located between the fascia and the skin of the patient's back.

A preferred expansible pedicle screw in accordance with the invention comprises a shaft having distal and proximal portions. The distal portion has threads adapted to be threaded into the medullary canal of a vertebral pedicle, and the proximal portion has threads adapted to engage internal threads of a tubular extension. At its proximal end, the tubular extension has means, engageable by a wrench, for rotating the extension relative to the shaft in a direction to increase the distance between the proximal end of the tubular extension and the distal end of the shaft. Means are also provided for connecting a rigid link to said proximal end of the extension, whereby the extension of the expansible pedicle screw can be connected to another pedicle screw. Preferably, the shaft has a lengthwise internal passage for receiving a guide pin, and the tubular extension has a threaded female recess communicating with the passage for receiving a threaded adapter. A plurality of holes is preferably provided in an end face of the tubular extension for receiving projections of a wrench.

In the assembled vertebral fixation device, which comprises at least two expansible pedicle screws, the threads of the extensions are engaged partway with the threads of the shafts so that engagement of the link with the extensions prevents the extensions from rotating relative the shafts in directions such as to shorten the lengths of the expansible pedicle screws. The device therefore eliminates the need to keep multiple adapters of different sizes on hand during surgery, avoids the problem of selecting an adapter having the proper length, and allows precise positioning of the connecting link.

In various percutaneous spinal procedures, including decortication of vertebral plates, insertion of bone grafts, removal of herniated disc material and resection of nuclear tissue, it is often desirable to utilize two cannulae at the same time, one for insertion of manipulative instrumentation, e.g. forceps, and the other for endoscopic observation. My U.S. Pat. No. 5,395,317, dated Mar. 7, 1995, describes such percutaneous spinal procedures, and specifically relates to a technique in which a guide attached to a first cannula is used to maintain a second cannula in parallel relation to the first cannula.

Still further objects of this invention include the simplification of such percutaneous spinal procedures by obviating the second cannula, and the simplification of the procedure for gaining access to the intervertebral disc.

In accordance with the invention, a specially designed cannula assembly is used. The cannula assembly comprises a cannula having a wall of uniform thickness defining a cylindrical inner passage having an oval cross section, and an oval obturator located within the oval, cylindrical inner passage. The obturator has a cylindrical outer wall with an oval cross-section and closely fits the cylindrical inner passage of the cannula. The obturator preferably has an internal passage for receiving a guide, and has a blunt end projecting from the distal end opening of the cannula.

The cannula assembly is introduced percutaneously through the back of a patient, and the obturator is removed. After removal of the obturator, by virtue of the oval cross-section of the cannula passage, two or more instruments, for example an arthroscope and a forceps, can extend through the cannula simultaneously.

The introduction of the oval cannula is preferably carried out by inserting an elongated, hollow sleeve percutaneously toward an intervertebral disc of a patient posterolaterally, while the sleeve has an obturator extending through it; removing the obturator from the sleeve, while leaving the sleeve in place; passing over the sleeve an assembly comprising a cannula having an lumen with an oval cross-section and an obturator having an oval cross-section conforming to the lumen of the cannula, the oval obturator having a longitudinal passage for receiving the sleeve; removing the oval obturator from the cannula, while leaving the cannula in place.

A trephine may be inserted through the cannula toward the intervertebral disc, to form a fenestration in the annulus fibrosis of the disc, and the cannula can then pass through the fenestration. Preferably, the longitudinal passage in the oval obturator is large enough to receive the trephine. This allows the trephine to be operated while the oval obturator in still in place in the cannula, for more accurate guidance of the trephine.

The annular fenestration may be performed, under direct arthroscopic visualization and magnification, by a long and thin handle knife which is introduced into the lumen of the oval cannula.

Other objects, details and advantages of the invention will be apparent from the following detailed description when read in conjunction with the drawings.

BRIEF DESCRIPTION OF THE DRAWINGS

FIG. 6 is an axial section of an expansible pedicle screw in accordance with the invention;

FIG. 7 is a top plan view of the expansible pedicle screw of FIG. 6;

FIG. 8 is an exploded view showing two expansible pedicle screws, a rigid connecting link, and adapters and nuts for securing the connecting link to the pedicle screws;

FIG. 9 is an elevational view of a sleeve for an obturator used in conjunction with an oval cannula in accordance with the invention;

FIG. 10 is an elevational view of the obturator;

FIG. 11 is a longitudinal section through an assembly consisting of the sleeve and obturator of FIGS. 9 and 10;

FIG. 12 is a longitudinal section through an oval obturator in accordance with the invention;

FIG. 13 is a bottom plan view of the oval obturator of FIG. 12;

FIG. 14 is an elevational view of an oval cannula in accordance with the invention;

FIG. 15 is a bottom plan view of the oval cannula of FIG. 14;

FIG. 16 is a longitudinal section through an assembly of the oval cannula and obturator of FIGS. 12–15; and FIG. 17 is an elevational view of a trephine used with the oval obturator of FIG. 16.

DETAILED DESCRIPTION

Figure 1:
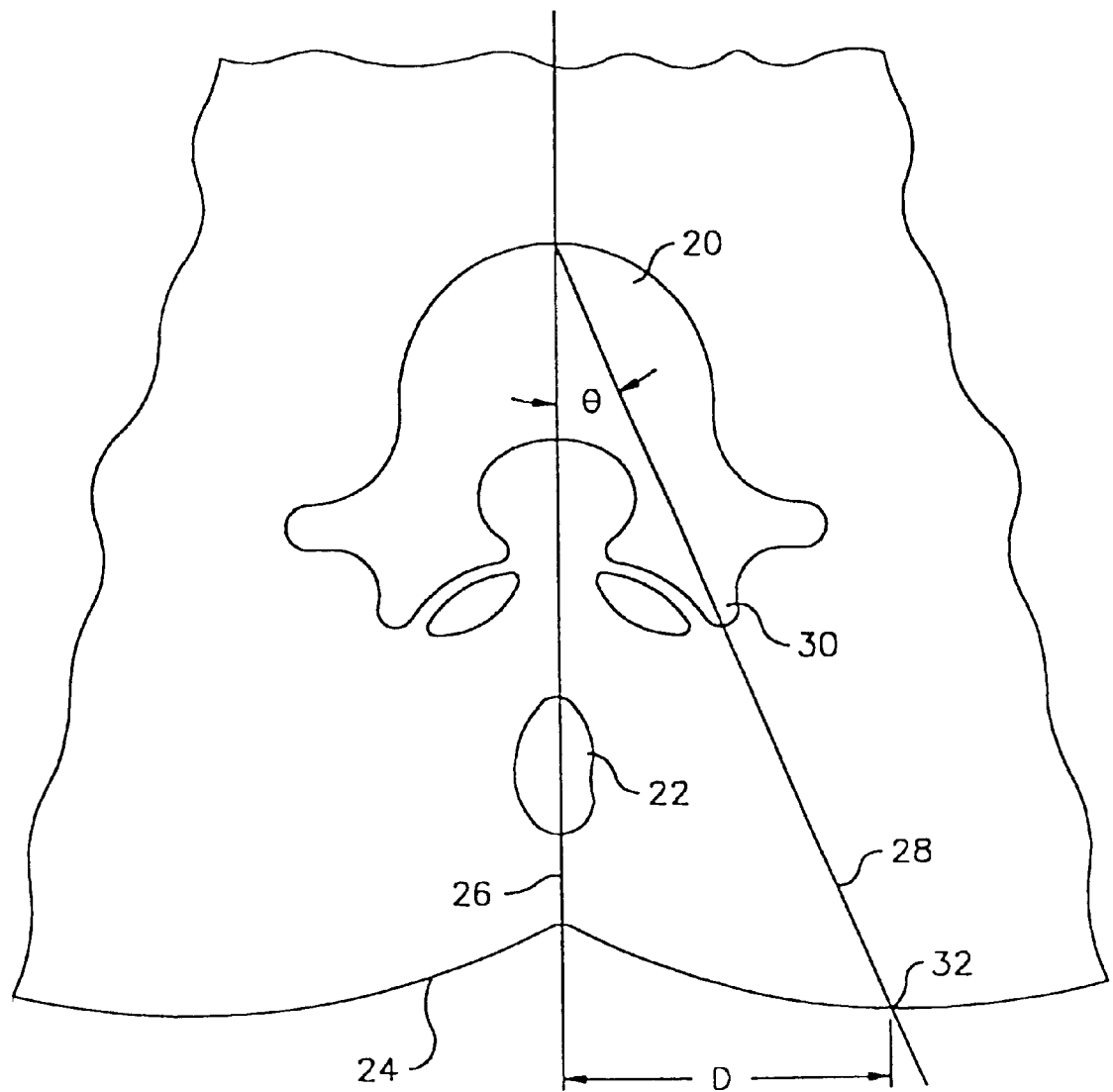
FIG. 1 is a schematic view depicting a CT scan through the pedicles of a lumbar vertebra, used for lateral location of an entry point and to establish an angle of approach through a pedicle.

The CT scan depicted in FIG. 1 shows a vertebral body 20 and a corresponding spinal process 22 in relation to the skin of the patient's back 24. A line 26 is drawn on the CT scan through the spinal process and through the center of the vertebral body. An oblique line 28 is drawn through the center of pedicle 30 to represent the desired path of entry of a guide pin. This line will normally, although not necessarily, intersect line 26 approximately at the point at which line 26 passes through the anterior surface of the vertebral body. A measurement is then taken of the distance D between line 26 and the point 32 at which line 28 intersects the skin of the patient's back. The approach angle θ between lines 26 and 28 is also measured by means of a protractor and noted. The same procedure is carried out on a CT scan of each of the one or more other vertebrae which are to be fixed to the vertebra shown in FIG. 1.

Either before or after the CT scans are taken, the patient is placed prone on a radiolucent frame and operating room table. The lumbar lordosis is flattened by flexion of the hips and the table, and care is taken to ensure that the patient is positioned symmetrically in relation to the frame and table. Then, a C-arm fluoroscope is positioned for anteroposterior radiographic visualization of the vertebral bodies at the surgical site. For improved visualization of the pedicles, the C-arm can be tilted away from the pedicles, for example at an angle of 10 degrees. However, the radiographic observation must be taken at the patient's midline.

Figure 2:
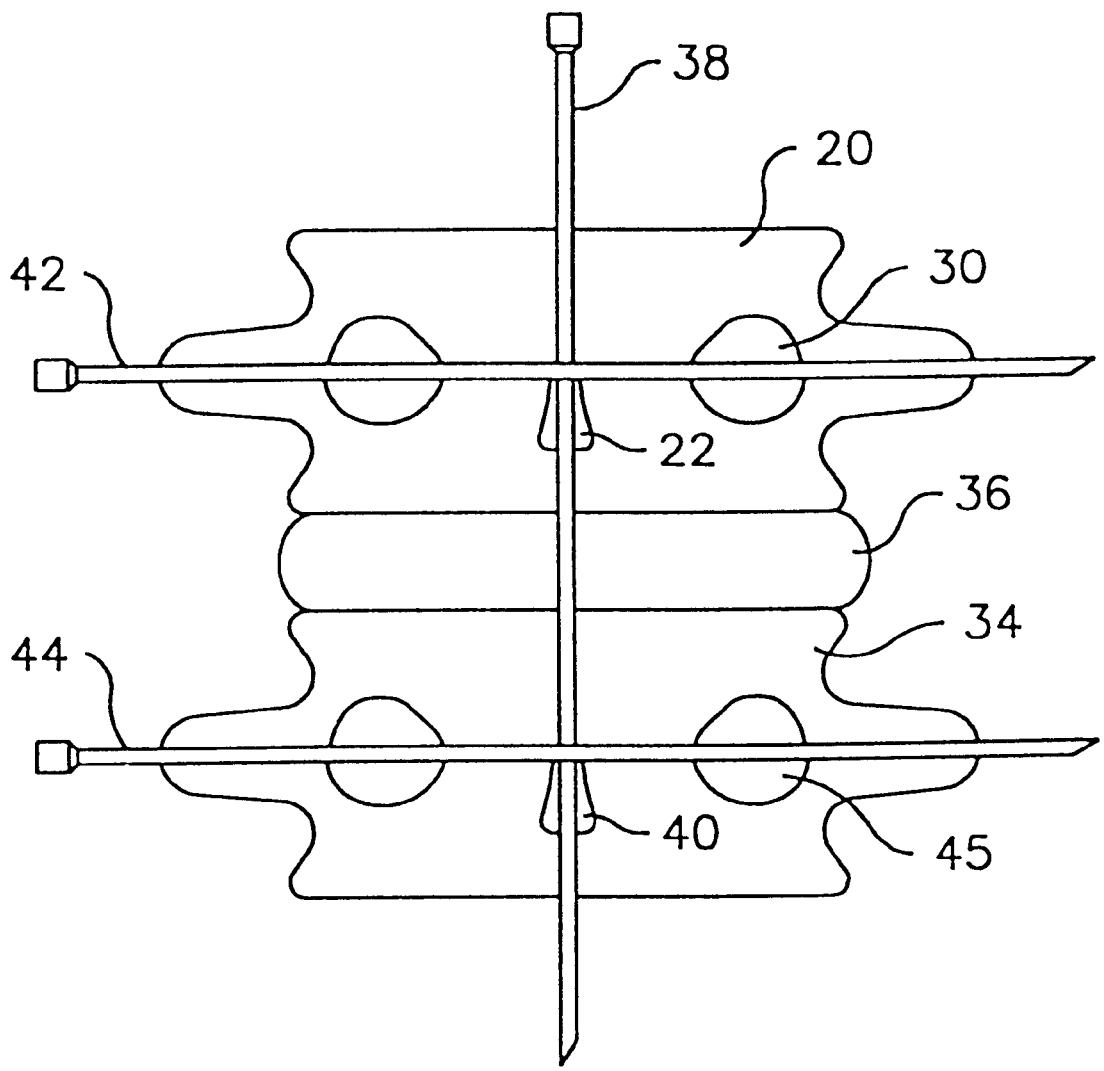
FIG. 2 is a schematic view depicting an anteroposterior fluoroscopic view of two adjacent vertebrae and their intervertebral disc, with radiopaque needles positioned on the patient's back for location of the entry points along the lengthwise direction of the spine.

The radiographic view of the patient's spine, as seen through a fluoroscope, is depicted in FIG. 2, where two adjacent vertebral bodies 20 and 34 are shown, with an intervertebral disc 36 between them. While observing the patient's spine through the fluoroscope, the surgeon places a first straight, narrow, radiopaque element 38, for example an 18 gauge needle, over the spinal processes 22 and 40. When the element 38 is properly positioned, the surgeon draws a vertical line in ink directly on the skin of the patient's back at a location corresponding to the position of the element 38. Similar radiopaque elements 42 and 44 are positioned over the centers of pedicles 30 and 45 respectively and arranged perpendicular to the direction of element 38. Horizontal ink lines are then drawn on the skin of the patient's back at locations corresponding to the locations of elements 42 and 44.

Figure 3:
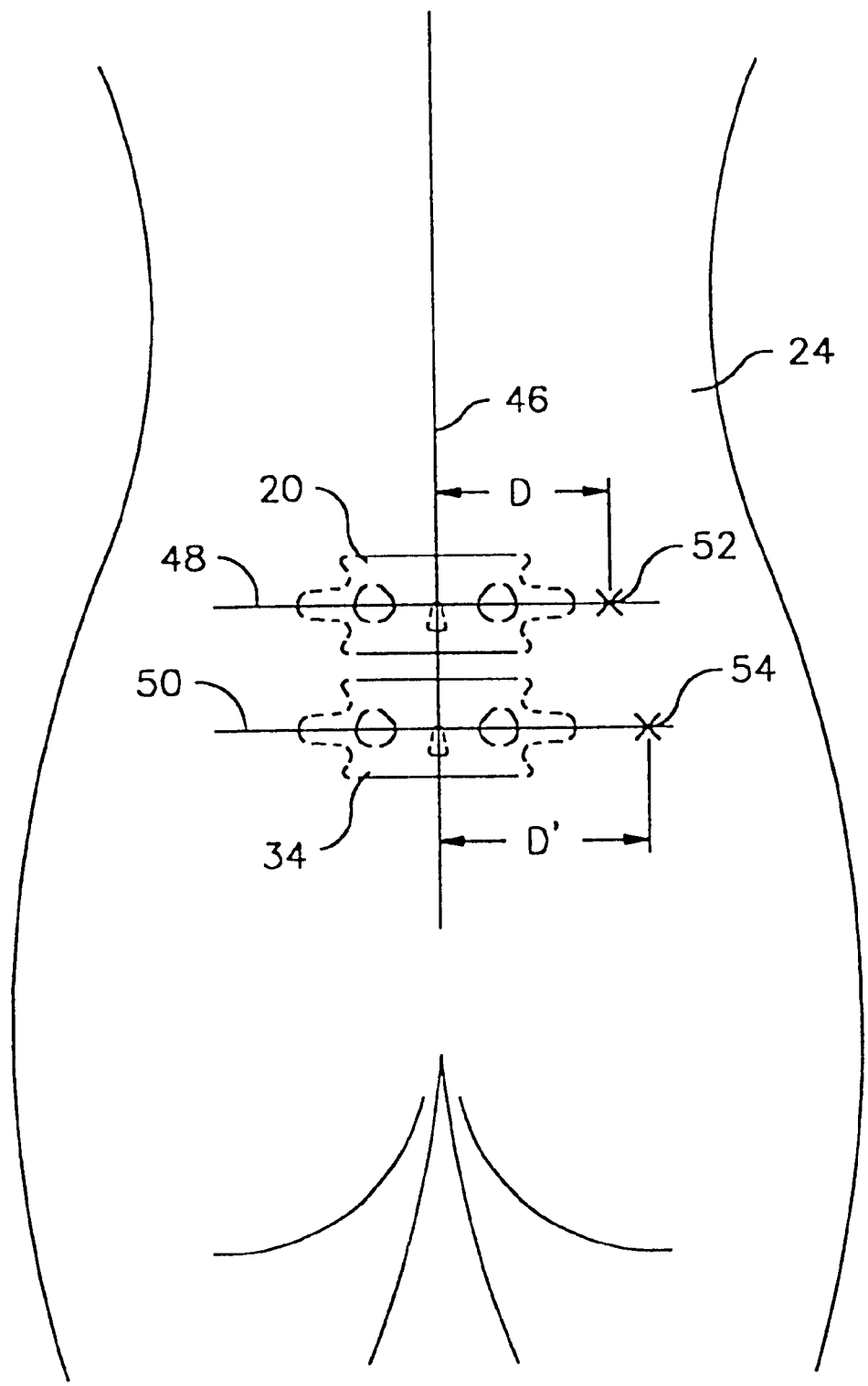
FIG. 3 is a schematic view of a patient's back, showing a vertical marking made over the spinal processes, two horizontal markings over the pedicles of adjacent vertebrae, and entry points on the horizontal markings.

As seen in FIG. 3, the ink lines on the patient's back 24 are shown at 46, 48 and 50. A first entry point mark 52 is made on horizontal line 48 at a distance D from the vertical line 46, the distance D having been previously measured on the CT scan through vertebral body 20 and pedicle 30. In a similar manner a second entry point mark 54 is made on horizontal line 50 at a distance D' from vertical line 46, D' having been measured on a CT scan of vertebral body 34.

Figure 4:
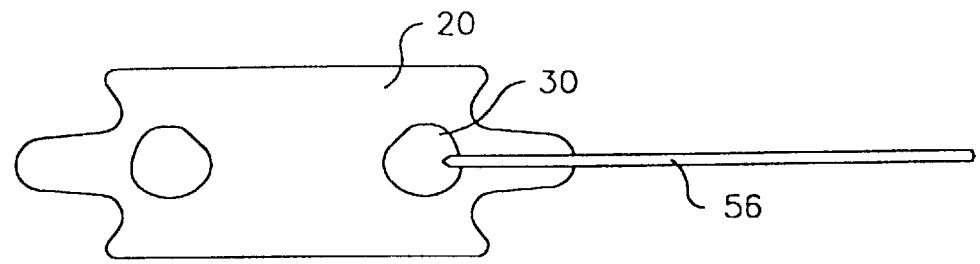
FIG. 4 is a schematic anteroposterior view of a vertebra showing the position of a guide pin in relation to a pedicle as the guide pin is about to enter the pedicle.
Figure 5:
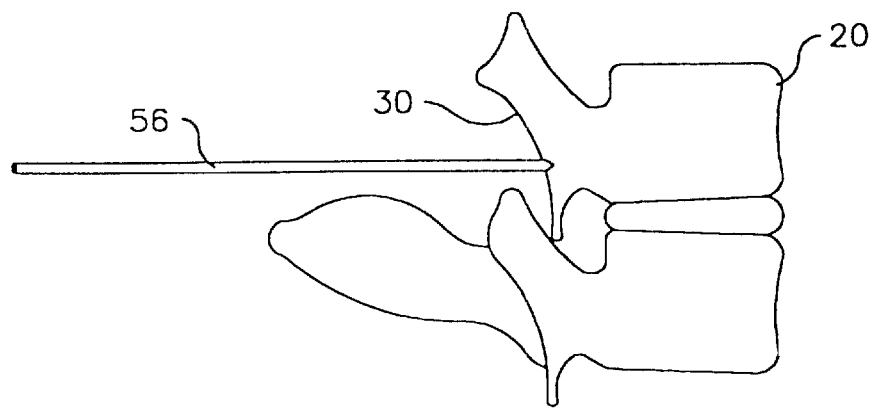
FIG. 5 is a schematic lateral view of the guide pin in relation to the pedicle as in FIG. 4.

Using a goniometer, a guide pin 56 (shown in FIGS. 4 and 5) is inserted through the skin at the entry point 52 (FIG. 3) and passed through the fascia until its tip reaches the pedicle 30 of vertebral body 20. The position of the tip of the guide pin, which should be just lateral to boundary of the pedicle 30 is verified by anteroposterior fluoroscopy as in FIG. 4, and appropriate adjustment can be made, if necessary. Likewise, the position of the pin in the middle of the pedicle and parallel to the vertebral plate is verified by lateral fluoroscopic observation, as in FIG. 5, and again adjustments can be made if necessary.

The guide pin 56 is then hammered into the pedicle and into the vertebral body. This is done for the corresponding pedicles of each of the vertebrae to be fixated. A protective cannula may be placed over the pedicle for protection and retraction of the paravertebral muscles while the medullary canal of the pedicle us being tapped. A sound is introduced to make certain that the cortex of the pedicle has not been violated.

After the medullary canal of the pedicle is prepared, a guide pin is inserted and a pedicle screw is passed over the guide pin and turned by a wrench until it passes the mid point of the anteroposterior diameter of the vertebra. The protective cannula may be left in place while the pedicle screw is being inserted.

The lengthwise expansible pedicle screw 58, which is shown in FIG. 6, comprises a shaft 60 having a distal portion 62 with threads adapted to be threaded into the medullary canal of a vertebral pedicle. The shaft 60 has a centrally located, multifaceted head 64 for engagement by a wrench, for example a hex wrench, and a proximal portion 66 having machine screw threads 68. A tubular extension 70 has internal threads 72, which are engaged with threads 68, so that rotation of the extension relative to the pedicle screw shaft 60, causes the extension to move lengthwise in one direction of the other, thereby increasing or decreasing the effective length of the pedicle screw 58. The threads 68 and 72 should fit each other with a close tolerance so that the extension and shaft form a rigid unit when they are locked against relative rotation.

The pedicle screw shaft 60 has an central passage 74 extending lengthwise through it along its axis of elongation. This central passage enables the shaft to be placed over a guide pin. The upper end of the tubular extension has a threaded recess 76, with a bottom opening 78 aligned with passage 74, enabling the guide pin to pass through upper end of the extension. As shown both in FIGS. 6 and 7, holes 80 and 82 are provided in upper end face 84 of the extension 70 for receiving projections of a special wrench for rotating the extension. The upper end of the extension 70 is also formed with wrench-engageable facets 85, which allow it to be held against rotation by a wrench as an adapter is attached to it. The facets 85 form a hex nut which is smaller than hex head 64, thus allowing an elongated socket wrench to be inserted over the extension 70 for engagement with hex head 64.

As shown in FIG. 8, the threaded recess 76 of the extension 70 is engageable with threads 86 of an adapter 88. The threads 86 extend downward from a plate 90. The plate has notches 92 and 94 for engagement by a special wrench used to tighten it into secure engagement with the extension 70. These notches are at opposite ends of a raised, part 96 of the plate, the raised part having parallel edges 98 and 100. The raised part 96 fits into a slot 102 in a link plate 104, and the adapter is secured to the link plate by a nut 106, which engages threads 108 which extend upwardly from the upper face of the adapter. The thickness of raised part 96 of the adapter is slightly less than the thickness of plate 104. Mating serrations 110 and 112 are provided on the adapter and on the link plate respectively.

FIG. 8 also shows an identical lengthwise expansible pedicle screw 58', which is connectible to a second rectangular slot 102' in link plate 104 by means of an adapter 88' and a nut 106'.

With the pedicle screws 58 and 58' inserted into the corresponding pedicles of adjacent vertebrae, the guide pins are removed. The extensions are then rotated counterclockwise by a special wrench inserted into the holes 80 and 82 (see FIG. 7) until the outer ends of the extensions are at a level above the lumbar fascia. With the extensions projecting above the lumbar fascia, their faceted outer ends can be engaged and held against rotation by another wrench so that adapters 88 and 88' can be attached. The adapters are secured by a special wrench engaged with their notches 92, 94, 92' and 94'. After the adapters are secured to the extension, further adjustment, if necessary can be carried out by rotating the adapters and extensions together. Then, through an appropriate incision, the link plate 104 is inserted and secured to the adapters. The link plate is located just above the surface of the lumbar fascia but below the skin.

The procedure for locating the insertion points and for determining the angle of approach for the guide pins provides for accurate placement of the pins and of the pedicle screws, eliminates the distortion inherent in previous methods, reduces the likelihood of damage to the vertebral structure, and produces generally superior and consistent results. The location procedure, using a combination of CT scanning and anteroposterior radiographic observation, is also usable for accurate determination of the insertion point and approach angle for a biopsy cannula and for various other procedures in which a spinal instrument is inserted percutaneously.

The lengthwise expansible pedicle screw is easily inserted and adjusted, and has as its principal advantage the fact that it eliminates the need to keep adapters of various lengths on hand for possible use in surgery.

For percutaneous spinal procedures such as decortication of vertebral plates, insertion of bone grafts, removal of herniated disc material and resection of nuclear tissue, the instrumentation depicted in FIGS. 8–17 can be used.

An obturator 114, shown in FIG. 10 is inserted into a guide sleeve 116, shown in FIG. 9, and the assembly of the obturator and sleeve, as shown in FIG. 11, is passed through the skin, subcutaneous tissue and muscle layer. The skin entry point can be determined by the size of the patient and a combination of CT scanning and anteroposterior and lateral radiographic observation in the same manner as in the case of the insertion of pedicle screws. Typically, the entry point is about 10–12 cm. from the midline. In an anteroposterior fluoroscopic projection, the tip of the obturator 114 is located either at the mid pedicle or lateral pedicle line. In a lateral fluoroscopic projection, the tip of the obturator and sleeve assembly should be touching a line drawn posterior to the backs of the vertebrae adjacent to the intervertebral disc which is being accessed.

An obturator 118, having a longitudinal passage 120 and a blunt end 122, as shown in FIGS. 12 and 13, is inserted into a cannula 124, as shown in FIGS. 14 and 15. The cannula has an oval cross-section, and the body of the obturator 118 also has an oval cross-section, conforming to the interior wall of the cannula. The major axis of the lumen of the cannula is preferably in the range of 7 to 12 mm, and the minor axis is preferably in the range of 3 to 5 mm. Thus, a typical cannula can have a 3×7 mm lumen, a 5×12 lumen, or even a 3×12 or 5×7 lumen.

The obturator 114 is removed from the sleeve 116, and the assembly of the cannula and obturator, as shown in FIG. 16, is passed over the guide sleeve 116 and directed toward the annulus fibrosis. The obturator and guide sleeve are then removed, leaving the cannula 124 in place.

A zero degree arthroscope is inserted to inspect the annular surface to make certain that neural structures are not in the path of the inserted cannula. After carrying out any necessary hemostasis, a trephine 126, shown in FIG. 17, is inserted through the passage in the obturator to sever the annular fibers, and the oval cannula is inserted into the fenestration formed by the trephine and engaged into the annular fibers. The trephine typically has an outer diameter of 4.5 mm.

The annular fenestration may also be performed, under direct arthroscopic visualization and magnification, by a long and thin handle knife which is introduced into the lumen of the oval cannula.

The oval cannula also may be used for the insertion of expandable cages which are utilized for fusion of the two adjacent vertebrae or the introduction of a disc prosthesis.

When the cannula is being used for the retrieval of herniated disc fragments, an attempt should be made to place the inner end of the inserted cannula adjacent to the spinal canal. In order to accomplish this, a zero degree arthroscope is inserted into the lumen of the oval cannula, and the inner end of the cannula is tilted toward the dorsum of the patient. This maneuver permits the visualization of the dura or the nerve root. At this time, the cannula is tilted ventrally and held against the annulus in preparation for annular fenestration and removal of herniated disc fragments.

When obtaining tissue from the vertebral bodies for biopsy and definitive diagnosis is desired, the steps which were described for insertion of a guide pin into the pedicle are followed by introduction of a cannulated drill with an outer diameter not exceeding 7 mm over the guide pin. The drill is driven through the medullary canal of the pedicle into the vertebral body of the desired vertebra.

A cannula is then inserted into the pedicle following the removal of the cannulated drill. Straight and upbiting biopsy forceps is passed through the cannula for harvesting of abnormal tissue.

The oval shape of the lumen of the cannula permits simultaneous introduction of an arthroscope and forceps for removal of herniated disc material and resection of nuclear tissue.

Where interbody fusion is to be attempted, another portal on the opposite side of the spine is necessary so that an auxiliary cannula can be introduced. However, this auxiliary cannula can be of comparatively small diameter, e.g. 5 mm. Curettes and reamers are passed through the oval cannula while an arthroscope, e.g. a 30 or 70 degree arthroscope is introduced into the intervertebral disc through the auxiliary cannula from the opposite portal. Decortication of the vertebral plates is carried out under direct arthroscopic magnification and illumination.

Autogenous bone, harvested from the patient's ilium, is passed through the cannulae and packed between the vertebral plates of the proximal and distal vertebrae. Afterwards, the instruments are withdrawn and the wound is closed.

The oval cannula has the advantage that it allows plural instruments, e.g. an arthroscope and a forceps to extend through it at the same time, thereby eliminating the need for a separate cannula on the same side of the spine as in U.S. Pat. No. 5,395,317. The oval cross-section is also advantageous in that it accommodates decorticators having blades with comparatively large lateral dimensions, e.g. 7 mm or 9 mm, for access to the concave surfaces of the vertebral plates. The decorticator can be rotated after the blades at its distal end pass beyond the opening at the distal end of the oval cannula. The use of the oval obturator allows the oval cannula to be introduced readily with a minimum number of steps, and provides guidance for the trephine used to fenestrate the annulus fibrosis of the disc.

Various modifications can be made to the instruments and procedures described herein. For example, the sequence in which the CT scans and the radiographic visualization take place can be reversed. Also, the structure of the longitudinally expansible pedicle screws can be modified, for example by providing for alternative shapes and configurations for the wrench-receiving elements 64 and 80 and 82. Various alternative forms of adapters and link plates or rods can also be used. Still other modifications may be made to the apparatus and method described above without departing from the scope of the invention as defined in the following claims.

I claim:

1. A cannula assembly for use in arthroscopic spinal surgery comprising a cannula having a wall of uniform thickness, the wall defining a cylindrical inner passage having an oval cross section, and an obturator located within said cylindrical inner passage, the obturator having a cylindrical outer wall with an oval cross-section and closely fitting the cylindrical inner passage of the cannula.

2. A cannula according to claim 1, wherein the obturator has an internal passage for receiving a guide.

3. A cannula according to claim 1, wherein the cannula has proximal and distal end openings and the obturator has a blunt end projecting from the distal end opening of the cannula.

4. A method of spinal surgery comprising the steps of introducing percutaneously through the back of a patient a cannula assembly comprising a cannula having a wall of uniform thickness, the wall defining a cylindrical inner passage having an oval cross section, and an obturator located within said cylindrical inner passage, the obturator having a cylindrical outer wall with an oval cross-section and closely fitting the cylindrical inner passage of the cannula, removing the obturator, and introducing at least two instruments through the cannula whereby said at least two instruments extend through the cannula simultaneously.

5. A method of spinal surgery according to claim 4, in which a fenestration is formed in the annulus fibrosis of a vertebral disc of the patient, in which the cannula is inserted into the fenestration, in which said at least two instruments include an arthroscope and a forceps, and in which herniated disc material is removed from the disc by means of the forceps.

6. A method of spinal surgery comprising the steps of:

inserting an elongated, hollow sleeve percutaneously toward an intervertebral disc of a patient posterolaterally, while the sleeve has an obturator extending through it;

removing the obturator from the sleeve, while leaving the sleeve in place;

passing over the sleeve an assembly comprising a cannula having an lumen with an oval cross-section and an obturator having an oval cross-section conforming to the lumen of the cannula, the obturator with the oval cross-section having a longitudinal passage for receiving the sleeve;

removing the obturator having the oval cross-section from the cannula, while leaving the cannula in place.

7. A method of spinal surgery according to claim 6, in which a fenestration is formed in the annulus fibrosis of said disc, and the cannula is inserted into the fenestration.

8. A method of spinal surgery according to claim 6, in which a trephine is passed through the cannula toward said intervertebral disc, a fenestration is formed in the annulus fibrosis of said disc by means of the trephine, and the cannula is inserted into the fenestration.

9. A method of spinal surgery according to claim 6, in which, prior to the removal of the obturator having the oval cross-section from the cannula, a trephine is passed through the longitudinal passage in the obturator toward said intervertebral disc, and a fenestration is formed in the annulus fibrosis of said disc by means of the trephine, and after the removal of the obturator having the oval cross-section from the cannula, the cannula is inserted into the fenestration.

10. A method of spinal surgery according to claim 6, in which, after removal of the obturator having the oval cross-section from the cannula, at least two instruments are introduced through the cannula whereby said at least two instruments extend through the cannula simultaneously.

11. A method of spinal surgery according to claim 6, in which, after removal of the obturator having the oval cross-section from the cannula, an arthroscope and a forceps are introduced through the cannula whereby the arthroscope and forceps extend through the cannula simultaneously, and herniated disc material is removed from the disc by means of the forceps.

12. A method of spinal surgery according to claim 6, in which a trephine is passed through the cannula toward said intervertebral disc, a fenestration is formed in the annulus fibrosis of said disc by means of the trephine, the cannula is inserted into the fenestration, and an arthroscope and a forceps are introduced through the cannula whereby the arthroscope and forceps extend through the cannula simultaneously, and herniated disc material is removed from the disc by means of the forceps.

13. A method of spinal surgery according to claim 6, in which, prior to the removal of the obturator having the oval cross-section from the cannula, a trephine is passed through the longitudinal passage in the obturator toward said intervertebral disc, a fenestration is formed in the annulus fibrosis of said disc by means of the trephine, and after the removal of the obturator having the oval cross-section from the cannula, the cannula is inserted into the fenestration, and an arthroscope and a forceps are introduced through the cannula whereby the arthroscope and forceps extend through the cannula simultaneously, and herniated disc material is removed from the disc by means of the forceps.

* * * * *